United States Patent [19]

Shah

[11] Patent Number: 5,443,466
[45] Date of Patent: Aug. 22, 1995

[54] METHOD AND APPARATUS FOR TREATING FRACTURES OF A BONE

[76] Inventor: Mrugesh K. Shah, 4314 Monte Video, Pasadena, Tex. 77504

[21] Appl. No.: 806,485

[22] Filed: Dec. 13, 1991

[51] Int. Cl.⁶ ............................................. A61B 17/56
[52] U.S. Cl. ........................................ 606/62; 606/72
[58] Field of Search ................ 606/62, 63, 64, 65, 606/66, 67, 68, 72–77

[56] References Cited

U.S. PATENT DOCUMENTS

| | | | |
|---|---|---|---|
| 3,670,724 | 6/1972 | Bosacco | 606/64 |
| 3,763,855 | 10/1973 | McAtee | 606/64 |
| 4,227,518 | 10/1980 | Aginsky | 606/63 |
| 4,262,665 | 4/1981 | Roalstad | 606/62 |
| 4,438,762 | 3/1984 | Kyle | 606/65 |
| 4,473,069 | 9/1984 | Kolmert | 128/92 B |
| 4,506,662 | 3/1985 | Anapliotis | 128/92 BC |
| 4,628,923 | 12/1986 | Medoff | 606/65 |
| 4,705,032 | 11/1987 | Keller | 606/62 |
| 4,913,137 | 4/1990 | Azer | 606/64 |
| 4,915,092 | 4/1990 | Firica et al. | 606/67 |
| 4,978,349 | 12/1990 | Frigg | 606/62 |
| 5,002,543 | 3/1991 | Bradshaw | 606/62 |

FOREIGN PATENT DOCUMENTS

| | | | |
|---|---|---|---|
| 2821785 | 11/1979 | Germany | 606/63 |
| 1514360 | 10/1989 | U.S.S.R. | 606/62 |

OTHER PUBLICATIONS

"The Uniflex Nailing System-Surgical Technique", Biomet Inc, Form No–Y–BMT–114/013189.

*Primary Examiner*—Michael A. Brown
*Attorney, Agent, or Firm*—Ben D. Tobor

[57] ABSTRACT

A nailing system, condylar anchor, and method for treating fractures of a bone include an intramedullary nail, whose lower end passes through a condylar anchor in a sliding and mating relationship, whereby the patient may exert weight upon the bone and relative movement between the intramedullary nail and condylar anchor is permitted.

31 Claims, 4 Drawing Sheets

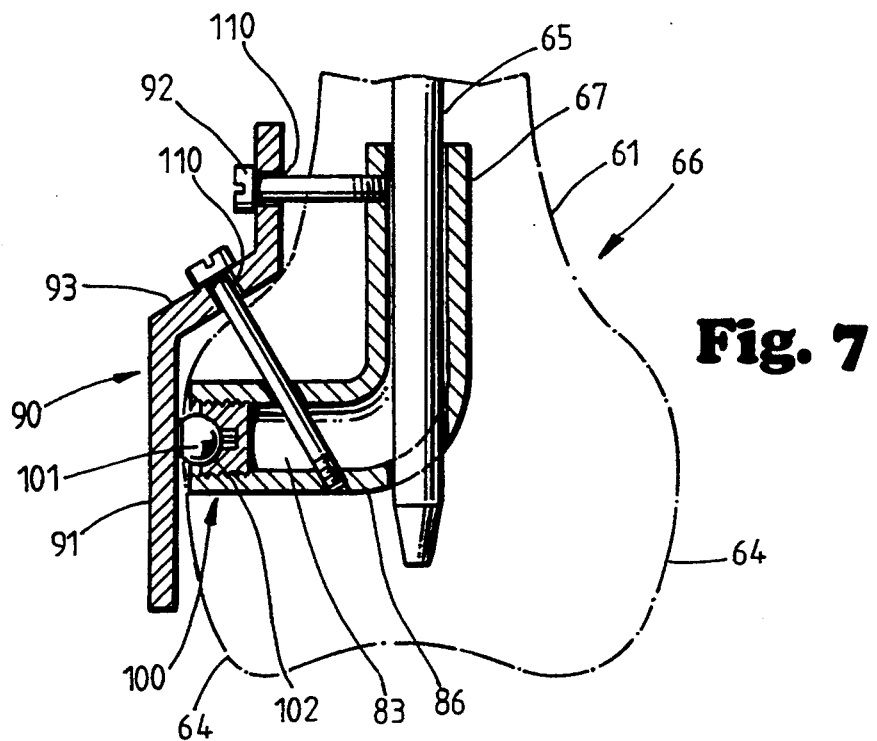
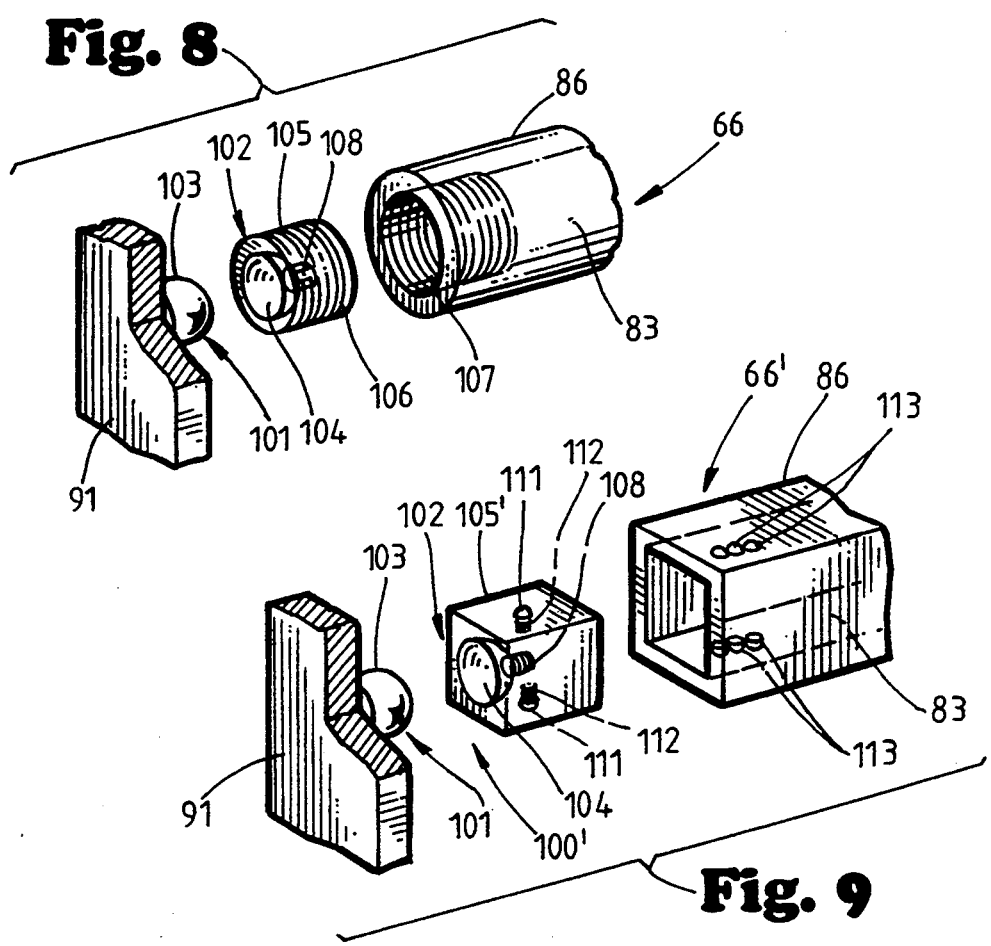

METHOD AND APPARATUS FOR TREATING FRACTURES OF A BONE

BACKGROUND OF THE INVENTION

1. Field of the Invention

The invention relates to a method and apparatus for treating fractures of a bone, in particular femurs or tibias having multiple and comminuted fractures therein. The apparatus includes a condylar anchor and a nailing system which includes an intramedullary nail to be used with the condylar anchor.

2. Discussion of the Prior Art

In the treatment of multiple and comminuted fractures in femurs and tibias, it is common practice to insert an intramedullary nail through the bone to treat such fractures. Typically, the intramedullary nail is secured within the bone by the placement of a plurality of fixation screws which are passed through the intramedullary nail and disposed at the upper and lower ends of the intramedullary nail. A disadvantage associated with these intramedullary nails is that the openings formed in the nail for the receipt of the fixation screws can create a weakened portion at the site of the opening, and the nail can fracture at the site of the openings and cause complications in the healing process, as well as additional surgical procedures to replace the damaged intramedullary nail and to implant a new intramedullary nail. Another disadvantage associated with previously proposed intramedullary nails and methods for treatment for fractures utilizing such nails, is that the patient is advised not to place any weight upon the damaged bone, although some forces being exerted upon the fractured bone at the interface of the fracture are believed to stimulate the natural fracture healing mechanisms.

Accordingly, prior to the development of the present invention, there has been no method and apparatus for the treatment of bone fractures which: permit an intramedullary nail to be used which does not have a plurality of openings formed at one end of the intramedullary nail; and permit the patient to place some weight on the fractured bone to thus compress the bone and stimulate the natural fracture healing mechanisms.

Therefore, the art has sought a method and apparatus for treating bone fractures which: utilize an intramedullary nail which does not have a plurality of openings formed at one of its ends for the receipt of one or more fixation screws; and permit the patient to place weight upon the fractured bone to compress the bone to stimulate the natural fracture healing mechanisms.

SUMMARY OF THE INVENTION

In accordance with the invention, the foregoing advantages have been achieved through the present nailing system for the treatment of fractures of a bone. The nailing system of the present invention includes: an intramedullary nail, the nail having a longitudinal axis and a cross-sectional configuration; and a condylar anchor, which includes an intramedullary nail receiving member having a passageway extending through the intramedullary nail receiving member, the passageway having a longitudinal axis and first and second ends and a cross-sectional configuration which permits the intramedullary nail to pass through the first end and beyond the second end of the passageway, the longitudinal axes of the passageway and the intramedullary nail being substantially parallel and coincident with each other; and means for positioning the intramedullary nail receiving member within the bone.

A further feature of the present invention is that the cross-sectional configuration of the passageway may conform to the cross-sectional configuration of the intramedullary nail, whereby the intramedullary nail may pass through the passageway in a substantially sliding and mating relationship. Another feature of the present invention is that the positioning means may include an elongate member, having a longitudinal axis, the elongate member extending outwardly and angularly from the intramedullary nail receiving member, and prevents rotational movement of the intramedullary nail receiving member within the bone. An additional feature of the present invention is that the longitudinal axis of the elongate member may be disposed substantially perpendicular to the longitudinal axis of the intramedullary nail receiving member, or it may be disposed at an angle with respect to the longitudinal axis of the intramedullary nail receiving member within a range of forty-five to ninety degrees.

A further feature of the present invention is that a means for securing the intramedullary nail receiving member to the bone may be provided, and the securing means may include a plate member which abuts against the elongate member and at least one screw which passes through the plate member. Another feature of the present invention is that the intramedullary nail may have first and second ends and has a tubular cross-sectional configuration, the first end having a threaded reinforcing sleeve disposed thereon, the second end of the intramedullary nail passing through the intramedullary nail receiving member of the condylar anchor. Another feature of the present invention is that the second end of the intramedullary nail has a smooth outer surface with no openings formed therein and no fixation screws passing therethrough.

A further feature of the present invention is that there may be provided a means for adjustably mounting the plate member with respect to the bone. Another feature of the present invention is that the adjustable plate mounting means may include an abutment member associated with the plate member and a mating abutment member associated with the elongate member, at least one of the abutment members being movable to provide variations in the angular disposition of the plate member with respect to the elongate member. Additional feature of the present invention is that the abutment member may be fixedly secured to the plate member and the mating abutment member may be movably and adjustably mounted within the elongate member.

In accordance with the present invention, the foregoing advantages have also been achieved through the present method for treating fractures of a bone, having an upper and a lower end, the bone having a medullary canal therein. The method of the present invention includes the steps of: disposing a condylar anchor in the medullary canal of the lower end of the bone, the condylar anchor including an intramedullary nail receiving member having a passageway extending therethrough; inserting, from the upper end of the bone, an elongate intramedullary nail, having an upper and a lower end, into the medullary canal; passing the intramedullary nail downwardly through the medullary canal and through the passageway in the condylar anchor; and permitting relative movement between the intramedullary nail and the condylar anchor.

A further feature of the present invention includes the step of fixating the upper end of the intramedullary nail to the upper end of the bone. An additional feature of the present invention includes the step of securing the condylar anchor to the lower end of the bone, while still permitting relative movement between the intramedullary nail and the condylar anchor.

In accordance with the present invention, the foregoing advantages have also been achieved through the present condylar anchor for use in a bone with an elongate intramedullary nail, the nail having a longitudinal axis and a cross-sectional configuration. The condylar anchor of the present invention includes: an intramedullary nail receiving member having a passageway extending through the intramedullary nail receiving member, the passageway having a longitudinal axis and first and second ends, and having a cross-sectional configuration which permits the intramedullary nail to pass through the first end and beyond the second end of the passageway, the longitudinal axis of the passageway and the intramedullary nail being substantially parallel and coincident with each other; and means for positioning the intramedullary nail receiving member within the bone.

The method and apparatus of the present invention, when compared with previously proposed intramedullary nails and methods for treatment of fractures of a bone, have the advantages of: not requiring openings disposed in one end of the intramedullary nail whereby fractures thereof are prevented; and permits the patient to place some weight upon the fractured bone to compress the bone fracture to stimulate the natural fracture healing mechanisms.

BRIEF DESCRIPTION OF THE DRAWINGS

In the drawings:

FIG. 7 is a partial cross-sectional view of the lower portion of a femur illustrating the condylar anchor of the present invention being utilized with an embodiment of a means for adjustably securing a plate member associated with the condylar anchor to a bone, in accordance with the present invention;

FIG. 8 is an exploded view of the securing plate member means of FIG. 7; and

FIG. 9 is an exploded view of another embodiment of a means for adjustably securing a plate member associated with the condylar anchor to a bone for use with the condylar anchor of FIG. 5.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined in the appended claims.

DETAILED DESCRIPTION OF THE INVENTION

Figure 1:
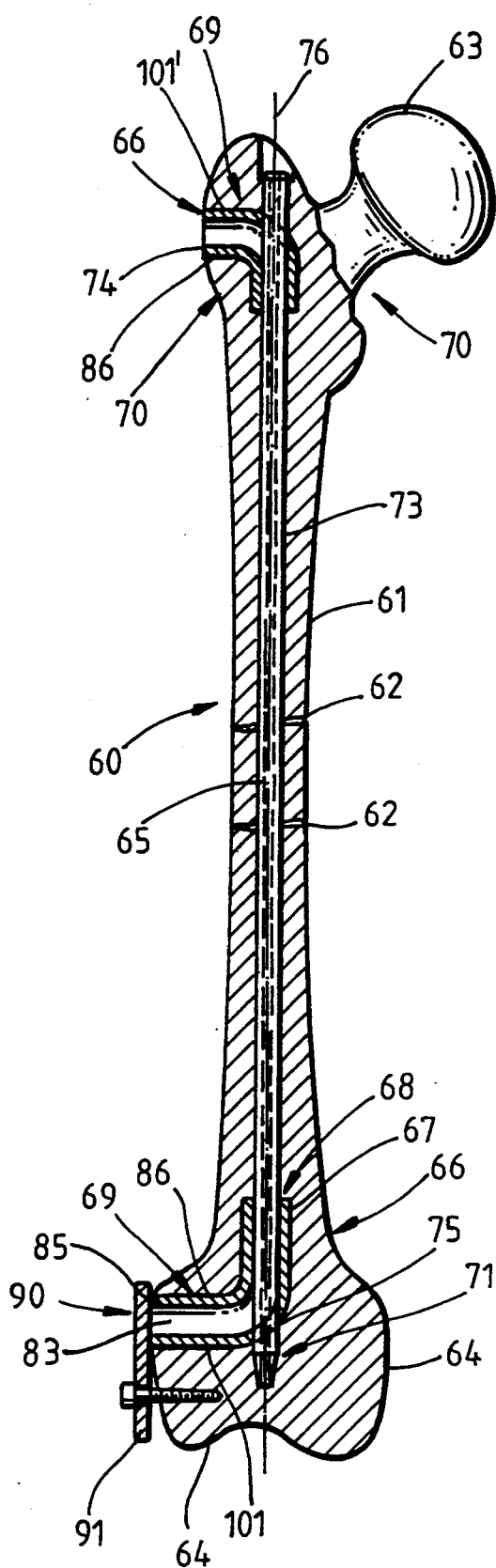
FIG. 1 is a partial cross-sectional view of a femur having an intramedullary nail and condylar anchor of the present invention disposed therein.
Figure 4:
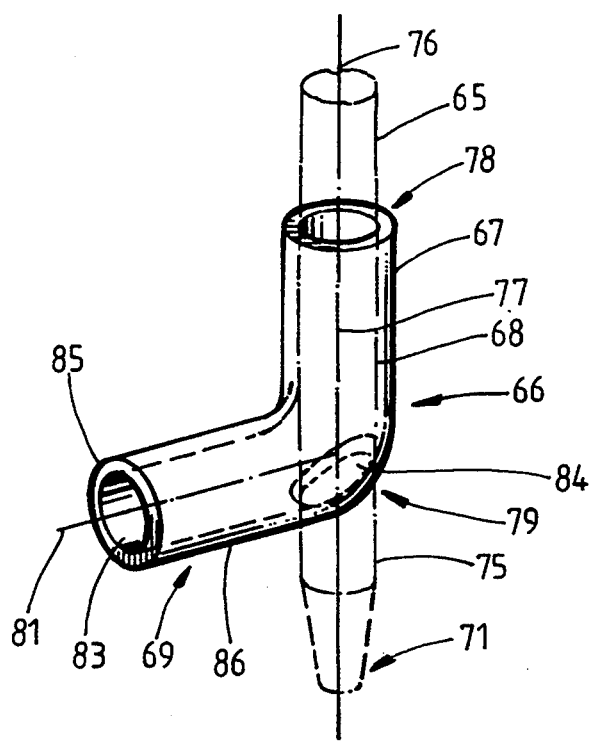
FIG. 4 is a perspective view of an intramedullary nail and condylar anchor in accordance with the present invention.

In FIGS. 1 and 4, a nailing system 60 in accordance with the present invention is shown in use with a bone 61 having multiple fractures 62 therein, bone 61 being illustrated as a femur having a trochanter 63 and two condyles 64 at the lower end of the femur 61. Nailing system 60, in accordance with the present invention, generally includes an intramedullary nail 65 and a condylar anchor 66 which includes an intramedullary nail receiving member 67 having a passageway 68 extending through the intramedullary nail receiving member 67, and means for positioning 69 the intramedullary nail receiving member 67 within the bone 61.

Figure 1A:
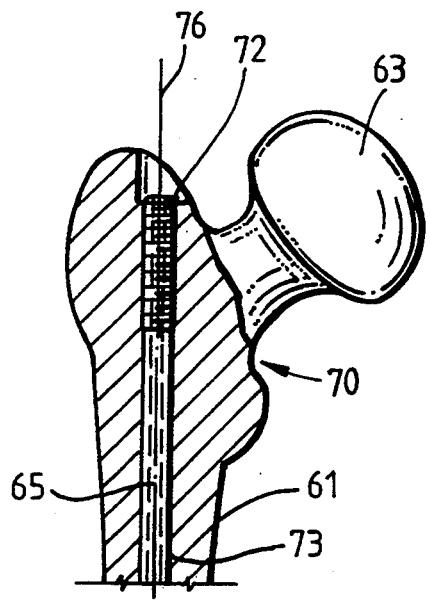
FIG. 1A is partial cross-sectional view of the trochanter of the femur of FIG. 1, wherein a reinforcing sleeve, in accordance with the present invention, is disposed on the upper end of the intramedullary nail.

Still with reference to FIGS. 1 and 4, intramedullary nail 65 has first and second ends 70, 71 and has a tubular cross-sectional configuration, with the first end 70 passing through another condylar anchor 66, which because it is disposed in the trochanter may also be referred to as a trochanter anchor 74. Trochanter anchor 74 has the same construction of condylar anchor 66, as to be hereinafter described in greater detail. Alternatively, as illustrated in FIG. 1A, the first end 70 of intramedullary nail 65 may have a threaded reinforcing sleeve 72 disposed thereon. The second end 71 of the intramedullary nail 65 passes through the intramedullary nail receiving member 67 of condylar anchor 66. Preferably intramedullary nail 65 is manufactured from stainless steel, titanium, or alloys thereof, or any other material having the requisite strength, durability, and compatibility characteristics necessary for an implant for bone 61. Threaded reinforcing sleeve 72 (FIG. 1A) may be threadedly received upon the upper end 70 of nail 65, or may be welded to, or formed integral with, the upper end 70 of nail 65. As will be hereinafter described in greater detail, threaded reinforcing sleeve 72 serves to fixedly secure nail 65 within the medullary canal 73 of bone 61, as well as provide reinforcing both to the upper end 70 of nail 65, as well to the upper end of bone 61.

Still with reference to FIGS. 1 and 4, the second, or lower, end 71 of intramedullary nail 65 has a smooth outer surface 75 with no openings formed therein and no fixation screws passing therethrough. As previously described, elimination of such openings and not passing fixation screws through the lower, or second, end 71 of intramedullary nail 65 substantially decreases the likelihood of a fracturing of the intramedullary nail 65 at its second, or lower, end 71. The longitudinal axis 76 of intramedullary nail 65 is shown to substantially lie parallel and coincident with the longitudinal axis of bone 61. It should be understood that the particular bone 61 being treated and the location of fractures 62 may influence the exact disposition of intramedullary nail 65 within bone 61. It should be further noted that nailing system 60 could be utilized for treatment of fractures in other bones 61, such as the tibia.

As seen in FIG. 4, the passageway 68 extending through condylar anchor 66 has a longitudinal axis 77 and first and second ends 78, 79 and a cross-sectional configuration which permits the intramedullary nail 65 to pass through the first end 78 and beyond the second end 79 of the passageway 68, with the longitudinal axis 76 of the intramedullary nail 65 and the longitudinal axis 77 of passageway 68 being substantially parallel and coincident with each other. Preferably the cross-sectional configuration of passageway 68 conforms to the cross-sectional configuration of intramedullary nail 65, whereby the intramedullary nail 65 passes through the passageway 68 in a substantially sliding and mating relationship, as illustrated in FIGS. 1–4. Preferably, when the cross-sectional configuration of intramedullary nail 65 is circular, the intramedullary nail receiving member 67 of condylar anchor 66 has a passageway 68 having a circular cross-sectional configuration, as illustrated in FIGS. 1–4. Alternatively, intramedullary nails 65 may be utilized having other cross-sectional configuration, such as a rectangular, cross-sectional configuration, as illustrated in FIG. 3A. Intramedullary nail 65' (FIG. 3A) while having an outer cross-sectional configuration of a rectangle, or square, is still preferably provided with a tubular passageway 80 extending along its longitudinal axis 76, as illustrated in the intramedullary nail 65' of FIG. 3A and the intramedullary nail 65 of FIG. 3. Primed reference numerals are utilized herein for elements of nailing system 60 which generally operate in the same manner and function and in the same manner as the corresponding elements denoted with unprimed reference numerals; however, the structure of the elements bearing primed numerals may differ somewhat. It should be noted that the four longitudinal edges 81 of intramedullary nail 65' of FIG. 3A still maintain the substantially sliding and mating relationship previously described when utilized with an intramedullary nail receiving member 67 having a circular shaped passageway 68. It should of course be readily apparent to one of ordinary skill in the art that the cross-sectional configuration of intramedullary nail 65 could be other than the square or rectangular cross-sectional configuration illustrated in FIG. 3A, and could include triangular, hexagonal, etc. shaped cross-sectional configurations.

Figure 3:
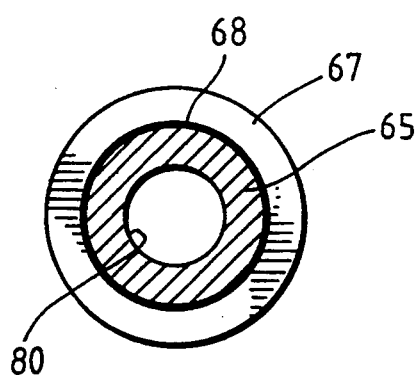
FIG. 3 is a cross-sectional view taken along line 3—3 of FIG. 2.
Figure 5:
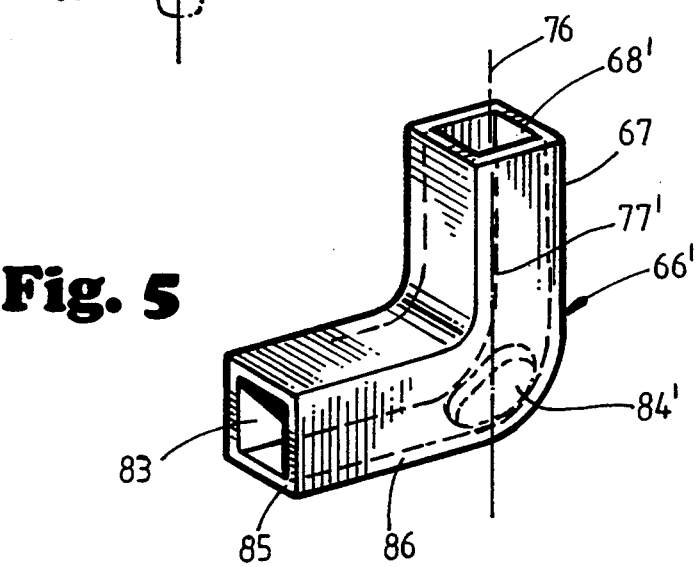
FIG. 5 is a perspective view of another embodiment of the condylar anchor in accordance with the present invention.

With reference to FIG. 5, a condylar anchor 66' is illustrated wherein the intramedullary nail receiving member 67 has a passageway 68' disposed therein, wherein the cross-sectional configuration of passageway 68' is square or rectangular. Condylar anchor 66' could be utilized with intramedullary nail 65 having a tubular cross-sectional configuration, as illustrated in FIG. 3, or could be used with an intramedullary nail 65' having a square or rectangular cross-sectional configuration, such as illustrated in FIG. 3A. Once again, the longitudinal axes 76 of the intramedullary nails 65, 65' would be disposed substantially parallel and coincident with the longitudinal axis 77' of passageway 68', with the intramedullary nails 65, 65' passing through the passageway 68' in a substantially sliding and mating relationship, as previously described.

Figure 2:
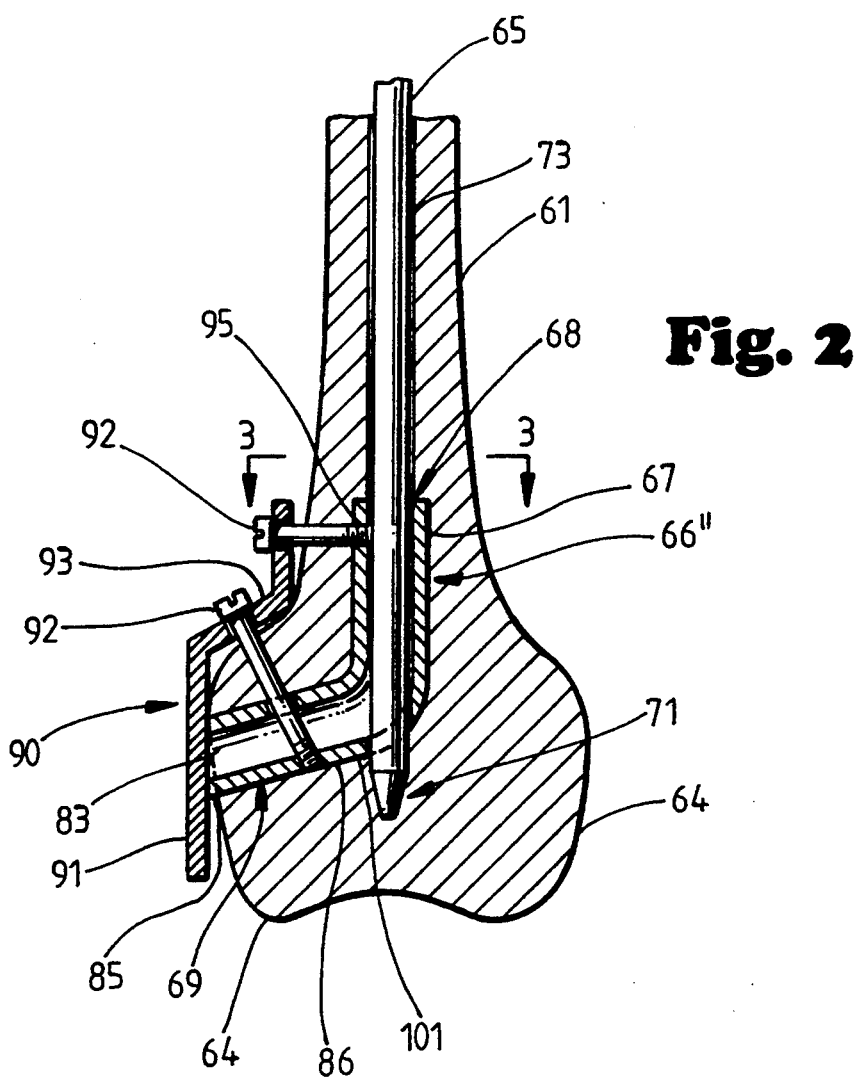
FIG. 2 is a partial cross-sectional view of the lower portion of a femur illustrating the condylar anchor of the present invention being utilized with an embodiment of a means for securing a plate member associated with the condylar anchor to a bone, in accordance with the present invention.
Figure 3A:
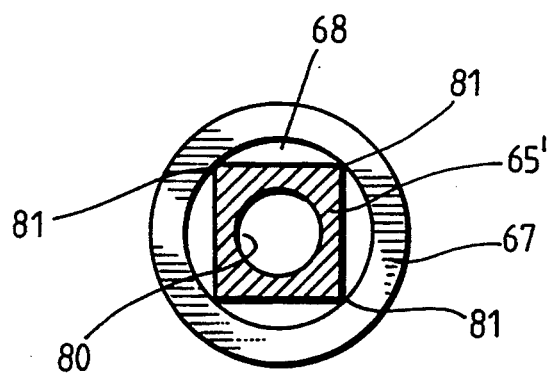
FIG. 3A is a cross-sectional configuration similar to that of FIG. 3, but illustrating an intramedullary nail having a rectangular, or square, cross-sectional configuration.

With reference to FIGS. 1, 2, and 4, positioning means 69 for intramedullary nail receiving member 67 preferably includes an elongate member 86 having a longitudinal axis 81 with the elongate member 86 extending outwardly and angularly from the intramedullary nail receiving member 67. As illustrated in FIGS. 1 and 4, elongate member 86 of positioning means 69 is disposed substantially perpendicular to the longitudinal axis 77 of the intramedullary nail receiving member 67, and the longitudinal axes 81, 77 of the elongate member 86 and the intramedullary nail receiver member 67 intersect with each other. Alternatively, dependent upon the bone 61 with which nailing system 60 is to utilized, the longitudinal axis 81 of elongate member 86 may be disposed at an angle with respect to the longitudinal axis 77 of intramedullary nail receiving member 67 within a range of forty-five to ninety degrees, as illustrated in FIGS. 2 and 6, with condylar anchor 66".

Figure 6:
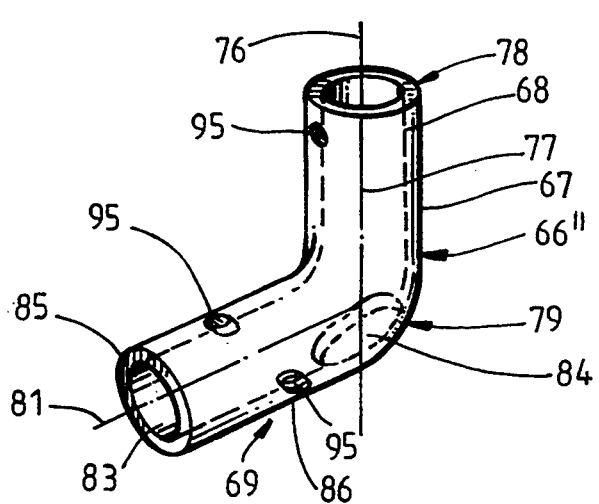
FIG. 6 is a perspective view of the embodiment of the condylar anchor illustrated in FIG. 2.

Preferably, elongate member 86 of positioning means 69 has the same cross-sectional configuration as the intramedullary nail receiving member 67 of anchors 66, 66', 66" as seen in FIGS. 4, 5 and 6. Thus, the elongate members 86 for the condylar anchors 66 of FIG. 4 and 66" of FIG. 6 have a circular cross-sectional configuration, and has a square or rectangular cross-sectional configuration in the case of the condylar anchor 66' of FIG. 5. Elongate members 86 are thus provided with an interior passageway 83 which intersects with passageways 68, 68' of condylar anchors 66, 66', 66". Condylar anchors 66, 66' can be manufactured from tubular stock material, in the case of anchors 66, 66" or rectangular shaped stock in the case of condylar anchor 66', and the stock material is bent to dispose elongate members 86 at the desired angular configuration with respect to passageways 68, 68'. Openings 84, 84' may be provided at the second, or lower, ends 79 of intramedullary nail receiving member 67 to accommodate the passageway of intramedullary nail 65 through the lower end 79 of condylar anchors 66, 66', 66". Opening 84 preferably has a circular cross-sectional configuration, and opening 84' may be either a circular or square or rectangular-shaped opening to accommodate the passing of intramedullary nails 65, 65' therethrough. Alternatively, condylar anchors 66, 66', 66" may be cast in the shapes illustrated in FIGS. 4, 5 and 6 in a conventional manner.

With reference to FIGS. 1 and 2, nailing system 60 may include a means for securing 90 intramedullary nail receiving member 67 to the bone 61. Securing means 90 may include a plate member 91 which abuts against the elongate member 86 and has at least one screw 92 which passes through the plate member 91 and is threadedly received in condyle 64 (FIG. 1) or in nail receiving member 67 (FIG. 2). Plate member 91 is disposed in an abutting relationship with the end 85 of elongate member 86. It should be noted that preferably screws 92 do not contact intramedullary nail 65, whereby intramedullary nail 65 may pass through passageway 68 of intramedullary nail receiving member 67 in a sliding and mating relationship, and relative movement between intramedullary nail 65 and the intramedullary nail receiving member 67 of condylar anchor 66, 66', 66" is permitted.

Alternatively, as illustrated in FIG. 2, plate member 91 may have a slight bend 93 formed therein which permits two screws 92 to pass through plate member 91, one screw 92 being threadedly received in intramedullary nail receiving member 67, the other screw being threadedly received within the elongate member 86 of positioning mean 69. As illustrated in FIG. 5, condylar anchors 66' may be provided with suitable threaded openings 95 for the receipt of screws 92.

The nailing system 60 and condylar anchors 66, 66', 66", in accordance with the present invention, may be used to treat fractures 62 of a bone 61 having a medullary canal 73 (FIGS. 1 and 2) therein in the following manner. After determining in a conventional manner the location of fractures 62, an incision is made in the skin (not shown) surrounding the lower end of the bone 61 adjacent the location at which it is desired to place condylar anchor 66, 66', 66". An opening 101 is made in the lower end of bone 61 of a sufficient size and depth so that condylar anchor 66, 66', 66" may be disposed in the medullary canal 73 of the lower end of the bone 61. Positioning means 69, or elongate member 86, may be grasped by the surgeon to assist him or her in positioning the intramedullary nail receiving member 67 of condylar anchor 66, 66', 66" within intramedullary canal 73. After condylar anchor 66, 66', 66" has been disposed at its desired location, an elongate intramedullary nail 65, 65' is inserted from the upper end of the bone 61 into the medullary canal 73, and nail 65, 65', is passed through the medullary canal 73 and through the passageway 68, 68' of the intramedullary nail receiving member 67 of anchor 66, 66', 66".

Intramedullary nail 65, 65' may be passed through medullary canal 73 in a conventional manner, as by reaming the medullary canal 73 to a desired diameter to accept the intramedullary nail 65, 65', the medullary canal 73 being preferably reamed to a diameter slightly larger than the nail 65, 65' to be implanted. The nail 65, 65' may then be driven in a conventional manner downwardly through the medullary canal 73. The intramedullary nail 65, 65' is passed through the passageway 68, 68' of condylar anchor 66, 66', 66", whereby the lower end 71 of intramedullary nail 65, 65' extends outwardly of intramedullary nail receiving member 67 and through opening 84, 84' into the general configuration illustrated in FIGS. 1 or 2. While intramedullary nail 65 is being passed into condylar anchor 66, 66', 66", positioning means 69, or elongate member 86, permits the surgeon to slightly move condylar anchor 66, 66', 66" so that the lower end 71 of intramedullary nail 65 may enter passageway 68, 68'. Relative movement between the intramedullary nail 65, 65' and the condylar anchor 66, 66', 66"is permitted, due to the sliding and mating relationship of intramedullary nail 65, 65' within passageway 68, 68' of intramedullary nail receiving member 67 of condylar anchor 66, 66', 66". The anchor 66, 66', 66" thus serves to prevent intramedullary nail 65, 65' from pivoting about its upper end 70, and permits intramedullary nail 65, 65' to provide the necessary rigidity and stability to bone 61. Positioning means 69, or elongate member 86, further prevents rotation of the intramedullary nail receiving member 67 and movement of nail 65, 65', due to the angular disposition of elongate member 86 with respect to intramedullary nail receiving member 67, and the fact that elongate member 86 passes through and is in an abutting relationship with opening 101 in bone 61.

The upper end 70 of intramedullary nail 65, 65' may also be fixated, if desired, in a conventional manner by at least one fixation screw (not shown). Condylar anchor 66, 66', 66" may be further secured to the lower end of bone 61 by use of the securing means 90 or plate member 91 and screws 92, as previously described, while still permitting relative movement between the intramedullary nail 65, 65' and the condylar anchor 66, 66', 66", as previously described. The incision made for the condylar anchor 66, 66', 66", and the incision, or incisions, made for inserting the intramedullary nail 65, 65' may then be closed in a conventional manner.

Alternatively, the upper end 70 of intramedullary nail 65 may be fixated with respect to the upper of bone 61 by use of the threaded reinforcing sleeve 72 (FIG. 1A) previously described. Preferably, threaded reinforcing sleeve 72 is only used with an intramedullary nail 65 having a circular cross-sectional configuration as seen in FIG. 3B, whereby intramedullary nail 65 may be rotated to thread the threaded reinforcing sleeve 72 into the upper end of bone 61. After condylar anchor 66, 66" has been disposed at its desired location, as previously described, an elongate intramedullary nail 65 is inserted from the upper end of the bone 61 into the medullary canal 73. Nail 65 is then passed downwardly through the medullary canal 73 and through the passageway 68 of the intramedullary nail receiving member 67 of anchor 66, 66". As previously described, the nail 65 may be driven in a conventional manner downwardly through the medullary canal 73. When the lower end of threaded reinforcing sleeve 72 enters the upper end of bone 61, intramedullary nail 65 is then rotated to thread the reinforcing sleeve 72 into the upper end of bone 61 into the configuration illustrated in FIG. 1A.

Alternatively, as illustrated in FIG. 1, the upper end of bone 61 may be provided with another condylar anchor 66, or trochanter anchor 74 in the following manner. Trochanter anchor 74 has the same construction as condylar anchor 66 of FIG. 4. An opening 101' is made in the upper end of bone 61 of a sufficient size and depth so that trochanter anchor 74 may be disposed in the medullary canal 73 of the upper end of bone 61. Positioning means 69, or elongate member 86 may be grasped by the surgeon to assist him or her in positioning the intramedullary nail receiving member 67 of trochanter anchor 74 within medullary canal 73. Trochanter anchor 74 may be disposed within the upper end of bone 61 either before or after the disposition of condylar anchor 66, 66" in the lower end of bone 61. After both anchor 74, and either anchor 66 or 66' have been disposed within bone 61, intramedullary nail 65, 65' is inserted from the upper end of bone 61 into the medullary canal 73, and nail 65, 65', is passed downwardly through passageway 68 of the intramedullary nail receiving member 67 of anchor 74, and then downwardly through the passageway 68, 68' of the intramedullary nail receiving member 67 of anchor 66, 66".

With reference to FIGS. 7 and 8, a means for adjustably mounting 100 the plate member 91 of intramedullary nail receiving member securing means 90 with respect to bone 61 is illustrated for use with condylar anchors 66, 66', or 66". If because of the shape of bone 61 and condyle 64, plate member 91 of securing means 90 does not satisfactorily conform to the general shape of bone 61 and condyle 64, as illustrated in FIG. 2, it may be desirable to provide for variations in the angular disposition of the plate member 91 with respect to the elongate member 86 of positioning means 69. Adjustable mounting means 100 for plate member 91 preferably includes an abutment member 101 associated with plate member 91 and a mating abutment member 102 associated with elongate member 86 of positioning means 69. At least one of the abutment members 101, 102 is movable in order to provide variations in the angular disposition of the plate member 91 with respect to elongate member 86 of positioning means 69. Preferably abutment member 101 associated with plate member 91 is a ball member 103 fixedly secure to plate member 91, and the mating abutment member 102 is a spherical-shaped recess 104 associated with elongate member 86, mating abutment member 102 being movably and adjustably mounted within the elongate member 86. Preferably, mating abutment member 102 is an insert member 105 having a threaded outer surface 106 which is threadedly received within mating threads 107 formed in passageway 83 of elongate member 86. Spherical-shaped recess 104 is formed in one end of insert member 105, ball-shaped member 103 being received within spherical-shaped recess 104 in a sliding and mating relationship. A recess 108 may be formed at the bottom of spherical-shaped recess 104, recess 108 being adapted to be engaged by a small screwdriver or allen hex key, whereby upon insertion of a suitable tool within recess 108, insert member 105 can be rotated to move insert member 105 inwardly or outwardly with respect to passageway 83 of elongate member 86. Alternatively, abutment member 101 could be movably and adjustably mounted with respect to plate member 91, and mating abutment member 102 could either be fixedly secured to elongate member 86, or movably and adjustably mounted with respect to elongate member 86.

After condylar anchor 66 or 66", having mating abutment member 102 associated therewith, is disposed within bone 61, as previously described, and after intramedullary nail 65 has been passed through intramedullary nail receiving member 67, as previously described, plate member 91 having abutment member 101 disposed thereon may then be laid against condyle 64 of bone 61, with abutment member 101 being received within spherical recess 104 of mating abutment member 102. Should plate member 91 not be satisfactorily disposed against condyle 64 and bone 61, plate member 91 may be removed, and insert member 105 may be moved either inwardly or outwardly with respect to passageway 83 of elongate member 86, whereby plate member 91, when repositioned as illustrated in FIG. 7, satisfactorily lays against, and conforms to the shape of condyle 64 and bone 61. The openings 110 formed in plate member 91 through which screws 92 pass are made sufficiently larger than the diameter of screws 92, whereby screws 92 may pass through plate member 91 and provide sufficient play to accommodate the desired angular variation of plate member 91 with respect to elongate member 86.

With reference to FIG. 9, a means for adjustably mounting 100' plate member 91 with respect to a condylar anchor 66' of FIG. 5 also includes a ball-shaped member 103 as an abutment member 101 and a mating abutment member 102 having a spherical-shaped recess 104 for receipt of ball-shaped member 103. Insert member 105' has a mating rectangular, or square, configuration which is received within passageway 83 of elongate member 86, and is movably and adjustably mounted within elongate member 86. Insert member 105' is provided with at least one, and preferably two, spring-biased balls 111 and springs 112 which are biased outwardly and adapted for engagement with at least one of a plurality of mating indentations 113 formed within the interior passageway of elongate member 86. Insert member 105' has a recess 108 disposed at the bottom of spherical-shaped recess 104 to accept a suitable tool which enables insert member 105' to be moved inwardly, or outwardly, with respect to passageway 83 of elongate member 86. As insert member 105' is pushed inwardly, or pulled outwardly, with respect to passageway 83, balls 111 are moved inwardly and outwardly with respect to insert member 105', until they are received within the desired indentation 113 which provides the desired location of insert member 105' within passageway elongate member 86. Adjustable mounting means 100' is then utilized in the same manner as adjustable mounting means 100 as previously described.

It is believed that shortly after such incisions have begun to heal or healed, a patient who has had bone 61 treated in the manner previously described may place some weight on bone 61 to thereby compress bone 61, and in particular compress the portions of bone 61 adjacent fracture 62 to stimulate the natural fracture healing mechanisms. As bone 61 is compressed, such movement is provided for by the fact that condylar anchor 66, 66', 66", permits relative movement between intramedullary nail 65, 65' and condylar anchor 66, 66', 66".

It is to be understood that the invention is not limited to the exact details of construction, operation, exact materials or embodiment shown and described, as obvious modifications and equivalents will be apparent to one skilled in the art; for example, the condylar anchor may be disposed at the upper end of some types of bones, and the lower end of the intramedullary nail could have a fixation screw disposed therein, or be provided with another condylar anchor. Accordingly, the invention is therefore to be limited only by the scope of the appended claims.

I claim:

1. A condylar anchor for use in a bone with an elongate intramedullary nail, the nail having a longitudinal axis, a smooth outer surface with no openings formed therein, and a cross-sectional configuration, comprising:
   an intramedullary nail receiving member having a passageway extending through the intramedullary nail receiving member, the passageway having a longitudinal axis and first and second ends, and having a cross-sectional configuration which permits the intramedullary nail to pass through the first end and beyond the second end of the passageway, the longitudinal axes of the passageway and the intramedullary nail being substantially parallel and coincident with each other;
   the passageway of the intramedullary nail receiving member along the longitudinal axis of the passageway being larger than the cross-sectional configuration of the intramedullary nail to permit relative movement between the intramedullary nail and the intramedullary nail receiving member; and
   means for positioning the intramedullary nail receiving member within the bone, the positioning means including an elongate member having a longitudinal axis, the elongate member extending outwardly and angularly from the intramedullary nail receiving member, and prevents rotational movement of the intramedullary nail receiving member within the bone.

2. The condylar anchor of claim 1, wherein the cross-sectional configuration of the passageway conforms to the cross-sectional configuration of the intramedullary nail, whereby the intramedullary nail passes through the passageway in a substantially sliding and mating relationship.

3. The condylar anchor of claim 2, wherein the cross-sectional configuration of the passageway is circular.

4. The condylar anchor of claim 2, wherein the cross-sectional configuration of the passageway is rectangular.

5. The condylar anchor of claim 1, wherein the longitudinal axis of the elongate member is disposed substantially perpendicular to the longitudinal axis of the intramedullary nail receiving member passageway.

6. The condylar anchor of claim 5, wherein the longitudinal axes of the elongate member and the intramedullary nail receiving member passageway intersect with each other.

7. The condylar anchor of claim 1, wherein the longitudinal axis of the elongate member is disposed at an angle with respect to the longitudinal axis of the intramedullary nail receiving member passageway within a range of forty-five to ninety degrees.

8. The condylar anchor of claim 1, further including means for securing the intramedullary nail receiving member to the bone.

9. The condylar anchor of claim 8, wherein the securing means includes a plate member which abuts against the elongate member and at least one screw which passes through the plate member.

10. The condylar anchor of claim 9, further including means for adjustably mounting the plate member with respect to the bone.

11. The condylar anchor of claim 10, wherein the adjustable plate mounting means includes an abutment member associated with the plate member and a mating abutment member associated with the elongate member, at least one of the abutment members being moveable to provide variations in the angular disposition of the plate member with respect to the elongate member.

12. The condylar anchor of claim 11, wherein the abutment member is fixedly secured to the plate member and the mating abutment member is movably and adjustably mounted within the elongate member.

13. A nailing system for the treatment of fractures of a bone comprising:
an intramedullary nail, the nail having a longitudinal axis, a smooth outer surface with no openings formed therein and a cross-sectional configuration; and
a condylar anchor, which includes an intramedullary nail receiving member having a passageway extending through the intramedullary nail receiving member, the passageway having a longitudinal axis and first and second ends, and a cross-sectional configuration which permits the intramedullary nail to pass through the first end and beyond the second end of the passageway, the longitudinal axes of the passageway and the intramedullary nail being substantially parallel and coincident with each other;
the passageway of the intramedullary nail receiving member along the longitudinal axis of the passageway being larger than the cross-sectional configuration of the intramedullary nail to permit relative movement between the intramedullary nail and the intramedullary nail receiving member;
means for positioning the intramedullary nail receiving member within the bone, the positioning means including an elongate member having a longitudinal axis, the elongate member extending outwardly and angularly from the intramedullary nail receiving member, and prevents rotational movement of the intramedullary nail receiving member within the bone.

14. The nailing system of claim 13, wherein the cross-sectional configuration of the passageway conforms to the cross-sectional configuration of the intramedullary nail whereby the intramedullary nail passes through the passageway in a substantially sliding and mating relationship.

15. The nailing system of claim 14, wherein the cross-sectional configuration of the passageway is circular.

16. The nailing system of claim 14, wherein the cross-sectional configuration of the passageway is rectangular.

17. The nailing system of claim 13, wherein the longitudinal axis of the elongate member is disposed substantially perpendicular to the longitudinal axis of the intramedullary nail receiving member passageway.

18. The nailing system of claim 17, wherein the longitudinal axes of the elongate member and the intramedullary nail receiving member passageway intersect with each other.

19. The nailing system of claim 13, wherein the longitudinal axis of the elongate member is disposed at an angle with respect to the longitudinal axis of the intramedullary nail receiving member passageway within a range of forty-five to ninety degrees.

20. The nailing system of claim 13, further including means for securing the intramedullary nail receiving member to the bone.

21. The nailing of claim 20, wherein the securing means includes a plate member which abuts against the elongate member and at least one screw which passes through the plate member.

22. The nailing system of claim 21, further including means for adjustably mounting the plate member with respect to the bone.

23. The nailing system of claim 22, wherein the adjustable plate mounting means includes an abutment member associated with the plate member and a mating abutment member associated with the elongate member, at least one of the abutment members being moveable to provide variations in the angular disposition of the plate member with respect to the elongate member.

24. The nailing system of claim 23, wherein the abutment member is fixedly secured to the plate member and the mating abutment member is movably and adjustably mounted within the elongate member.

25. The nailing system of claim 13, wherein the intramedullary nail has first and second ends and has a tubular cross-sectional configuration, the first end having a threaded reinforcing sleeve disposed thereon, the second end of the intramedullary nail passing through the intramedullary nail receiving member of the condylar anchor.

26. The nailing system of claim 25, wherein the second end of the intramedullary nail has a smooth outer surface with no openings formed therein and no fixation screws passing therethrough.

27. A method for treating fractures of a bone having an upper and a lower end, the bone having a medullary canal therein, comprising the steps of:
disposing a condylar anchor in the medullary canal of the lower end of the bone, the condylar anchor including an intramedullary nail receiving member having a passageway extending therethrough, the passageway having a longitudinal axis;
inserting, from the upper end of the bone, an elongate intramedullary nail, having an upper and a lower end and a cross-sectional configuration, into the medullary canal,
the passageway of the intramedullary nail receiving member along the entire longitudinal axis of the passageway being larger than the cross-sectional configuration of the intramedullary nail and adapted to permit relative movement between the intramedullary nail and the intramedullary nail receiving member;

passing the intramedullary nail downwardly through the medullary canal and through the passageway in the condylar anchor; and permitting relative movement between the intramedullary nail and the condylar anchor.

28. The method of claim 27, further including the step of fixating the upper end of the intramedullary nail to the upper end of the bone.

29. The method of claim 27, further including the step of securing the condylar anchor to the lower end of the bone, while still permitting relative movement between the intramedullary nail and the condylar anchor.

30. The method of claim 27, further including the step of preventing rotation of the intramedullary nail receiving member within the bone.

31. The method of claim 30, wherein the rotation of the intramedullary nail receiving member is prevented by angularly disposing an elongate member attached to the intramedullary nail receiving member, the elongate member being disposed within an opening formed in the bone.

* * * * *